US009072823B2

United States Patent
Hopman et al.

(10) Patent No.: US 9,072,823 B2
(45) Date of Patent: Jul. 7, 2015

(54) SAFETY NEEDLE (71) Applicant: The Seaberg Company, Inc., Wilsonville, OR (US)

(72) Inventors: Lance D. Hopman, Tigard, OR (US); Lane M. Johnson, Chandler, AZ (US)

(73) Assignee: The Seaberg Company, Inc., Wilsonville, OR (US)

( * ) Notice: Subject to any disclaimer, the term of this patent is extended or adjusted under 35 U.S.C. 154(b) by 0 days.

(21) Appl. No.: 13/896,026

(22) Filed: May 16, 2013

(65) Prior Publication Data

US 2013/0310750 A1 Nov. 21, 2013

Related U.S. Application Data (60) Provisional application No. 61/647,629, filed on May 16, 2012, provisional application No. 61/665,851, filed on Jun. 28, 2012.

(51) Int. Cl.
*A61M 1/00* (2006.01)
*A61M 25/06* (2006.01)
*A61M 1/04* (2006.01)
(Continued)

(52) U.S. Cl.
CPC ............ *A61M 1/008* (2013.01); *A61M 25/0643* (2013.01); *A61M 2005/3212* (2013.01); *A61M 5/321* (2013.01); *A61M 1/04* (2013.01); *A61B 17/3474* (2013.01); *A61B 17/3496* (2013.01)

(58) Field of Classification Search
CPC ................. A61M 2005/3212; A61M 25/0643; A61M 5/321
USPC .............. 604/22, 158–163, 164.01, 272, 263, 604/171, 506
See application file for complete search history.

(56) References Cited

U.S. PATENT DOCUMENTS 4,869,717 A * 9/1989 Adair ............................ 604/506
4,991,988 A 2/1991 Snell et al.
(Continued)

FOREIGN PATENT DOCUMENTS

CA 2764552 7/2012
EP 0429390 7/1996
(Continued)

OTHER PUBLICATIONS

Purple Surgical, Ultimate Veress Needle, found at http://www.purplesurgical.com/index.php?option=com_content&task=view&id=52&Itemid=136, United Kingdom, 2012.
(Continued)

*Primary Examiner* — Theodore Stigell
*Assistant Examiner* — Amber Stiles
(74) *Attorney, Agent, or Firm* — Chernoff Vilhauer McClung & Stenzel LLP (57) ABSTRACT

A medical device including a portion similar to a Veress needle, useful for relief of tension pneumothorax. The device includes a hollow tubular stylet disposed movably within a hollow needle or cutting cannula, and an optionally releasable locking mechanism for keeping the stylet in place protruding distally beyond the sharpened distal end of the cutting cannula to prevent puncture of internal organs after the chest wall has been intentionally punctured. The stylet can also be moved outward from within the cannula to push a plug of tissue from the bore of the cannula. A valve or a connector for a tube may be provided at a proximal end of the stylet.

14 Claims, 6 Drawing Sheets

(51) Int. Cl.
*A61M 5/32* (2006.01)
*A61B 17/34* (2006.01)

(56) References Cited

U.S. PATENT DOCUMENTS

| | | | |
|---|---|---|---|
| 5,098,388 A | 3/1992 | Kulkashi et al. | |
| 5,316,013 A | 5/1994 | Striebel | |
| 5,320,608 A * | 6/1994 | Gerrone | 604/117 |
| 5,364,365 A | 11/1994 | Wortrich | |
| 5,374,252 A | 12/1994 | Banks et al. | |
| 5,578,053 A * | 11/1996 | Yoon | 606/185 |
| 5,685,852 A | 11/1997 | Turkel | |
| 6,102,920 A * | 8/2000 | Sullivan et al. | 606/147 |
| 6,447,483 B1 * | 9/2002 | Steube et al. | 604/158 |
| 6,626,868 B1 * | 9/2003 | Prestidge et al. | 604/158 |
| 6,656,160 B1 | 12/2003 | Taylor et al. | |
| 6,837,872 B2 * | 1/2005 | Crawford | 604/110 |
| 7,169,114 B2 | 1/2007 | Krause | |
| 8,321,167 B2 | 11/2012 | Haijima et al. | |
| 8,357,104 B2 | 1/2013 | Moos et al. | |
| 8,840,588 B2 | 9/2014 | Clement et al. | |
| 2002/0062104 A1 | 5/2002 | Ashby | |
| 2004/0073139 A1 | 4/2004 | Hirsch | |
| 2005/0261581 A1 | 11/2005 | Hughes | |
| 2009/0062744 A1 | 3/2009 | Weilbacher et al. | |
| 2009/0118639 A1 | 5/2009 | Moos et al. | |
| 2009/0171610 A1 | 7/2009 | Haijima et al. | |
| 2009/0192444 A1 | 7/2009 | Albrecht et al. | |
| 2009/0247952 A1 | 10/2009 | Weilbacher et al. | |
| 2009/0326476 A1 | 12/2009 | Carlyon | |
| 2009/0326561 A1 | 12/2009 | Carroll | |
| 2010/0274081 A1 | 10/2010 | Okoniewski | |
| 2012/0197078 A1 | 8/2012 | Stanley | |
| 2012/0209167 A1 * | 8/2012 | Weber et al. | 604/26 |
| 2013/0153632 A1 | 6/2013 | Hartoumbekis | |

FOREIGN PATENT DOCUMENTS

| | | |
|---|---|---|
| EP | 0546769 | 3/1997 |
| EP | 2231233 | 9/2010 |
| JP | 2010253270 A | 11/2010 |
| WO | WO 2009/140399 A2 | 11/2009 |

OTHER PUBLICATIONS

Office Depot, Foray Soft-Grip Retractable Gel Pens, on-line catalog (found at http://www.officedepot.com/a/products/510216/FORAY-Soft-Grip-Retractable-Gel-Pens/), 2013, United States.

* cited by examiner

SAFETY NEEDLE

BACKGROUND OF THE INVENTION

The present invention relates to treatment of medical conditions such as tension pneumothorax and particularly to a device for its treatment.

The U.S. military services currently prescribe needle decompression for treatment of tension pneumothorax, a condition which can be fatal if not quickly relieved. The means of treatment for prehospital care should be compact and as simple as practical.

The needle prescribed by the military services is sharp, creating the possibility of damaging underlying organs after initial penetration through the chest wall. It has been reported as well that the needle occasionally plugs with a tissue "core" as it travels through the chest wall. If the plug is detected, the needle could be flushed using a syringe; however it is not certain that the plug would be detected. A 3.15 inch long, 14 gauge angiocatheter needle is used as the standard of care for the U.S. military. Although the catheter is 14 gauge (0.083" diameter), the inner diameter is 0.058", and the needle outer and inner diameters are 0.058" and 0.042" respectively. This small inner diameter of 0.042" does not provide an effective means for venting pressurized air quickly from the pleural space. Removal of the needle, leaving the catheter in place, allows better flow, but is not desired, since if it were left in place for long periods it would in essence be an open pneumothorax, and because the catheter is likely to kink and close itself off. The military has considered adopting a 10 gauge needle (outer diameter 0.134"=3.404 mm, inner diameter 0.106"=2.692 mm) to permit greater flow, but it has been found that a larger gauge needle has more propensity to clog with a tissue core.

The Veress needle is a special needle used in laparoscopic surgical procedures. A conventional Veress needle consists of a hollow outer cannula ground obliquely to a sharp point at a distal end, and terminating in a plastic housing at the opposite proximal end. Enclosed within the outer cannula is a hollow tube that has a blunt tip at its distal end (common to the sharp tip of the outer cannula), and that is axially spring-biased in a distal direction by a spring contained in the plastic housing. When no force is applied to the distal end to resist the penetrating point, the spring bias forces the hollow inner tube to protrude just beyond the sharp tip of the outer cannula, obscuring the sharp tip and thereby protecting underlying organs from damage. When a force which overcomes the spring bias is applied to its distal end, as when the Veress needle is being pushed through a patient's abdominal wall, the inner tube is driven back within the outer cannula, exposing the sharp needle tip.

A Veress needle of this conventional configuration may be prone to at least the following shortcomings:

(1) Such a needle may not adequately protect a patient if, when the needle is introduced subcutaneously in the vicinity of vital organs (which is often the case), there is a force of sufficient magnitude to overcome the spring bias of the inner tube and thus expose the outer cannula's sharp tip.

(2) Such a needle may be prone to clogging, as the generally weak spring bias may be insufficient to overcome the resistive forces of tissue or blood which then may become wedged within the hollow outer cannula.

(3) The sharp tip of the Veress needle after use is another potential danger on the battlefield and is a challenge for the military.

Kulkashi (U.S. Pat. No. 5,098,388) discloses a Veress needle containing a mounted fluid transfer means such as a bobbin that moves out from the proximal end of a distal handle of the device when the needle is penetrating tissue, and that retracts into the handle when the needle has passed through the tissue and the inner tube moves in a distal direction to expose its distal end beyond the sharpened end of the hollow needle. The bobbin portion can be manually moved for repetitively retracting and extending the inner tube, in a manner causing the gas exit hole to wipe against an edge of the needle point, theoretically clearing the gas exit hole in the distal end of the inner tube.

SUMMARY OF THE INVENTION

The present application provides answers to some of the mentioned shortcomings of previously available devices, and discloses a safety needle device including similarities to a Veress needle, for emergency treatment of a tension pneumothorax, as defined by the appended claims that form a part of this disclosure.

An aspect of the safety needle device disclosed herein is that it prevents iatrogenic injury to underlying organs during needle decompression.

In one embodiment of the device disclosed herein, a safety needle includes a mechanism for optionally extending, locking, and unlocking its central tubular stylet.

One embodiment of the device disclosed herein can incorporate one of many various "retracting pen" mechanisms. In such a configuration, a hollow outer cannula is ground obliquely to a sharp point at its distal end, and its proximal end is mounted in a pen-like housing. Disposed within the outer cannula is a protective hollow inner tubular stylet with a blunt tip at the end common to the sharp tip of the outer cannula, and axially spring-biased via a spring contained in the pen-like housing.

An indicator in one embodiment of the device disclosed herein allows confirmation of correct needle placement.

In one embodiment, there is a hollow needle or cannula, and a hollow tube inside the needle, connected with a "pen click" mechanism which allows the sharp point of the device to be exposed or obscured through user action. This allows a user to be sure that the sharp tip of the needle cannot injure tissues when the tip is in the body and the mechanism is locked, and also allows the user to store the used needle without a container without the concern of sharps management.

In one embodiment, such a device has a plunger mechanism for dislodging a tissue plug from the needle. Since this device allows a tissue core to be dislodged, in one embodiment the needle or cannula could be of a fairly large diameter, such as 10 gauge, to assure ample fluid flow for relieving tension pneumothorax.

In one embodiment, a colored indicator is visible through a transparent side portion of the device, showing whether the needle is placed correctly, is not through the chest wall or is plugged with a tissue core.

The foregoing and other objectives and features of the invention will be more readily understood upon consideration of the following detailed description of the embodiments taken in conjunction with the accompanying drawings.

DETAILED DESCRIPTION OF PREFERRED EMBODIMENTS

Figure 1:
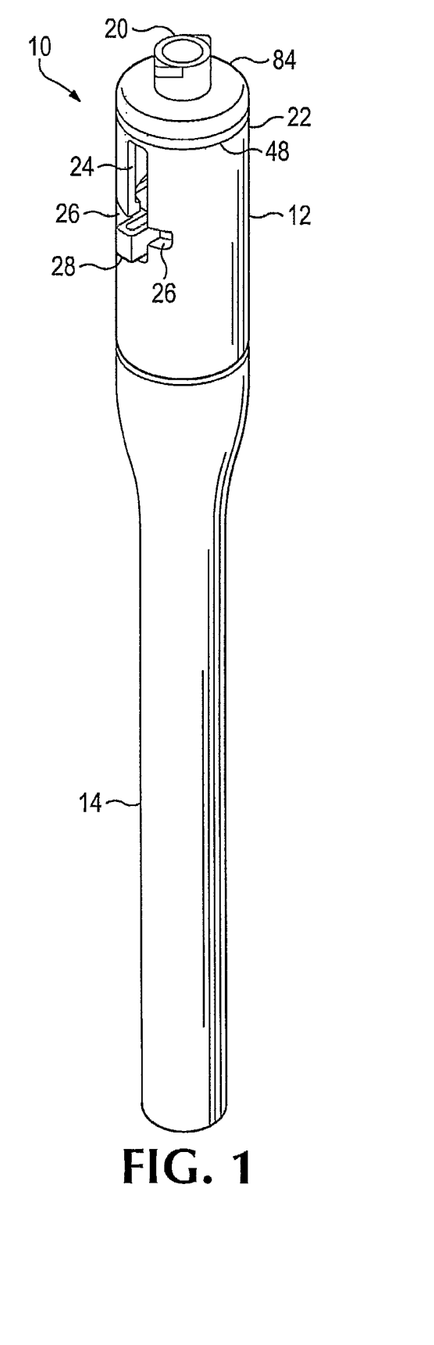
FIG. 1 is an isometric view of a medical instrument useful for emergency relief of tension pneumothorax according to the disclosure herein, together with a protective case.
Figure 2:
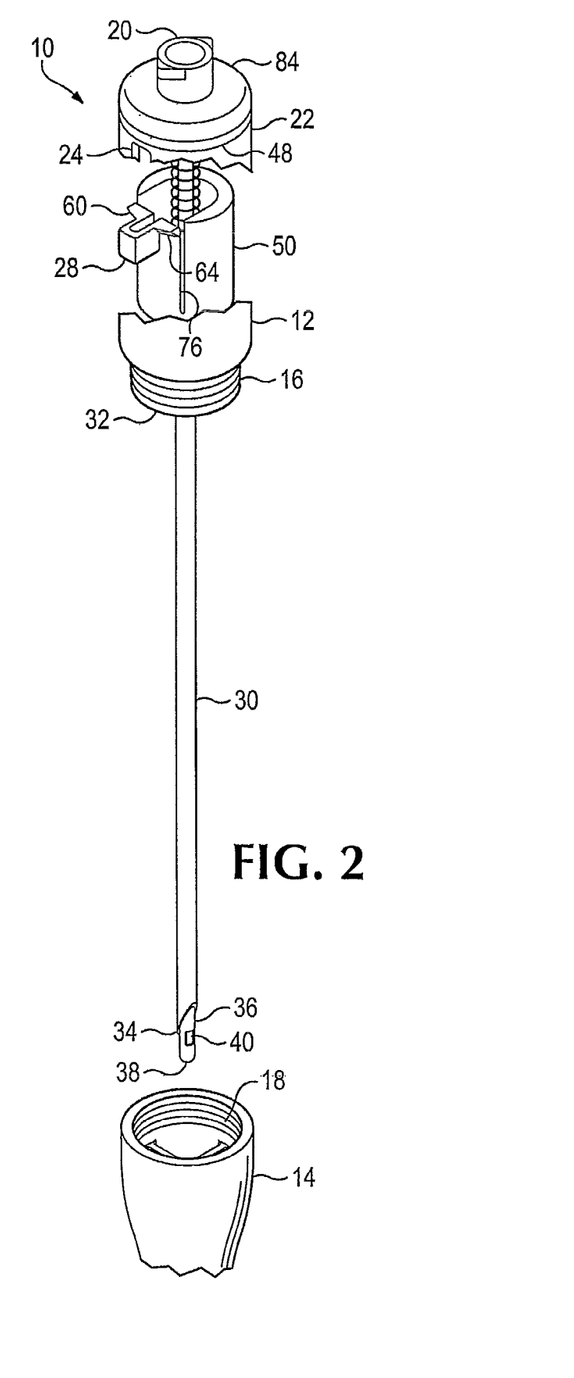
FIG. 2 is a partially cut-away view of the medical instrument shown in FIG. 1, taken from the same point of view, showing the protective case removed to expose a sharpened cannula and an associated hollow tubular stylet.

Referring to the drawings which form a part of the disclosure herein, and referring first to FIGS. 1 and 2, a medical device 10 includes a housing or body 12 to which a generally cylindrical protective outer cover 14 is shown connected in FIG. 1. The cover 14 may be detachably connected to the body 12 as by an externally threaded portion 16 of the body 12 and mating internal threads 18 in the cover 14. Both the body 12 and the cover 14 may be of suitable molded plastic. The device 10 may be packaged in a hard protective case for sterilization and protection in an austere prehospital environment.

A connector, such as a female Luer fitting 20, may be provided at the proximal end 22 of the body 12, the top end as shown in FIGS. 1 and 2. The body 12 may be generally cylindrical, and defines a slot 24 extending longitudinally along one side near the proximal end 22. The slot 24 pierces the cylindrical wall of the body 12, extending into the interior of the body 12, as will be explained more fully presently. A crosswise or transverse slot 26 intersects the longitudinal slot 24 near its distal end and extends a short distance on each side of the longitudinal slot 24. A latch release button 28 extends radially outward from the body 12 through the longitudinal slot 24.

As shown in FIG. 2, a hollow needle or cannula 30 extends from the distal end 32 of the body 12 along a central longitudinal axis of the body 12 and has a sharpened, oblique point 34.

Disposed within the cannula 30 is a hollow inner tube or tubular stylet 36 that has a blunt distal end or tip 38 and defines an opening 40 located close to the distal tip 38 and extending through the wall of the stylet 36 into its interior bore. With a cannula 30 of 10 gauge size, the bore of the stylet 36 may have an inside diameter 41 of 0.071", for example.

Figure 3:
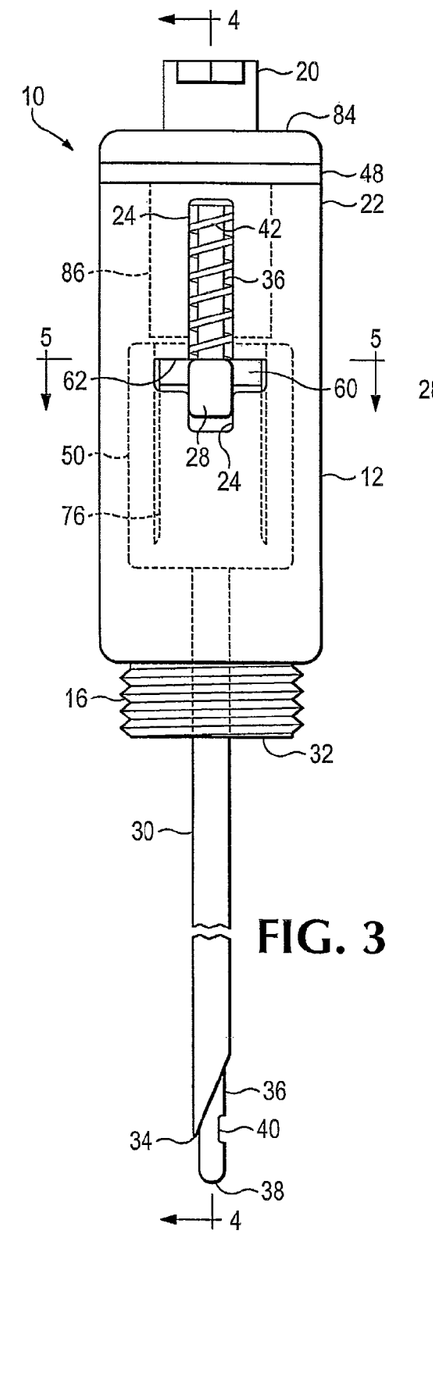
FIG. 3 is a front elevational view of the medical instrument shown in FIGS. 1 and 2, at an enlarged scale, with the cannula and tubular stylet shown foreshortened.
Figure 4:
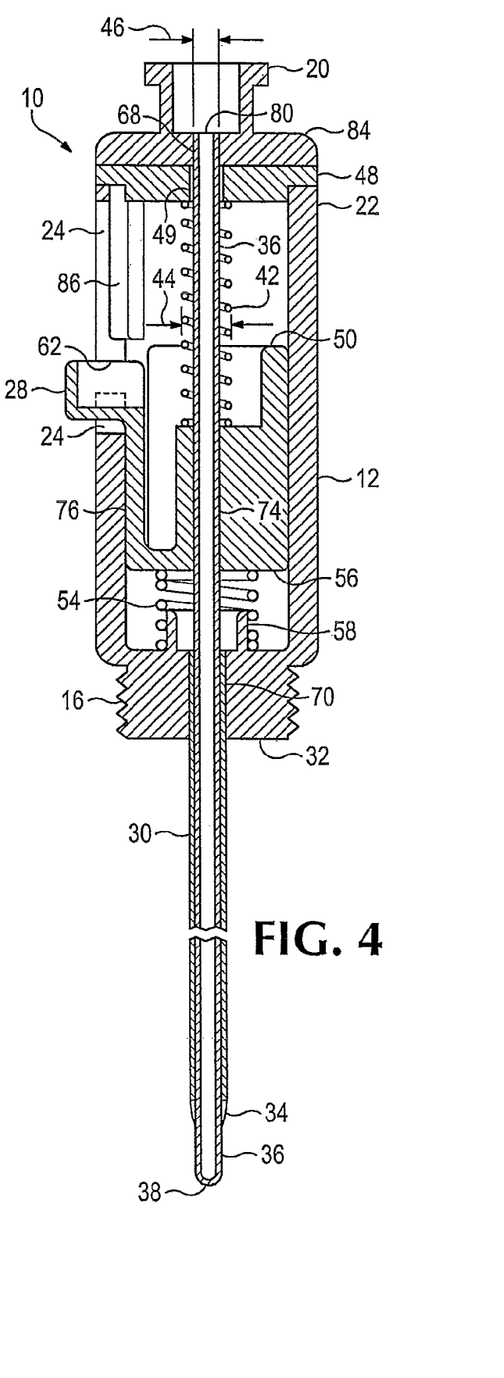
FIG. 4 is a sectional view taken along line 4-4 in FIG. 3.
Figure 5:
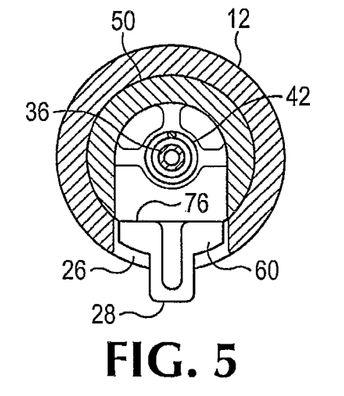
FIG. 5 is a sectional view taken along line 5-5 in FIG. 3.

Referring now also to FIGS. 3 and 4, the inner protective tubular stylet 36 continues through the plastic housing 12 and out at the top or proximal end 22 of the body 12. The proximal end 80 of the inner tubular stylet 36 extends into and is secured to the pushbutton 84, from which the connector or Luer fitting 20, if included, extends. Within the body 12, the hollow tubular stylet 36 passes through a helical compression spring 42 with a diameter 44 only slightly larger than the outer diameter 46 of the inner tubular stylet 36. One end of the spring 42 is lodged against the inner face of an end cap 48 closing the proximal end 22 of the body 12. The end cap 48 defines a central opening 49 through which the stylet 36 extends and is free to slide. The other end of the spring 42 presses against a carrier, or stylet pusher 50, slidingly disposed within the body 12, so that the spring 42 urges the stylet pusher 50 in a distal direction within the interior of the body 12. Another helical compression spring 54 is located within the interior of the body 12, between the distal end 32 and a distal face 56 of the stylet pusher 50. The spring 54 may have a larger diameter and is a stiffer spring than the spring 42. The spring 54 may be disposed around a cylindrical base or locater 58 extending inward from the distal end of the body 12 and around the stylet 36, so as to keep the spring 54 centered around the stylet 36. The spring 54 may be fitted tightly around the cylinder 58, at least at its distal end, or adhesively fastened to the cylinder 58.

As shown in FIG. 4, the stylet pusher 50 is held in a lower or distal location within the interior of the housing or body 12 by a locking mechanism including a pair of arms 60 extending from the latch release button 28 and engaged with a retaining surface 62 within the transverse slot 26, which functions as a latch receptacle for the arms 60. With the stylet pusher 50 in that position, the spring 54 is compressed and urges the stylet pusher 50 toward the proximal end 22 of the body 12, keeping the arms 60 of the locking mechanism engaged against retaining surfaces 62 of the proximal side of the transverse slot 26.

The body 12 may be molded around the proximal end of the cannula 30 as at 70, or the cannula 30 may be adhesively secured in the distal end portion 32 of the body 12. The inner tubular stylet 36 is movable axially within the cannula 30, and the carrier or stylet pusher 50 is fastened to the inner tubular stylet 36 at 74 so as to move together with it, as by being overmolded onto the stylet 26, or by being adhesively attached to it.

Figure 6:
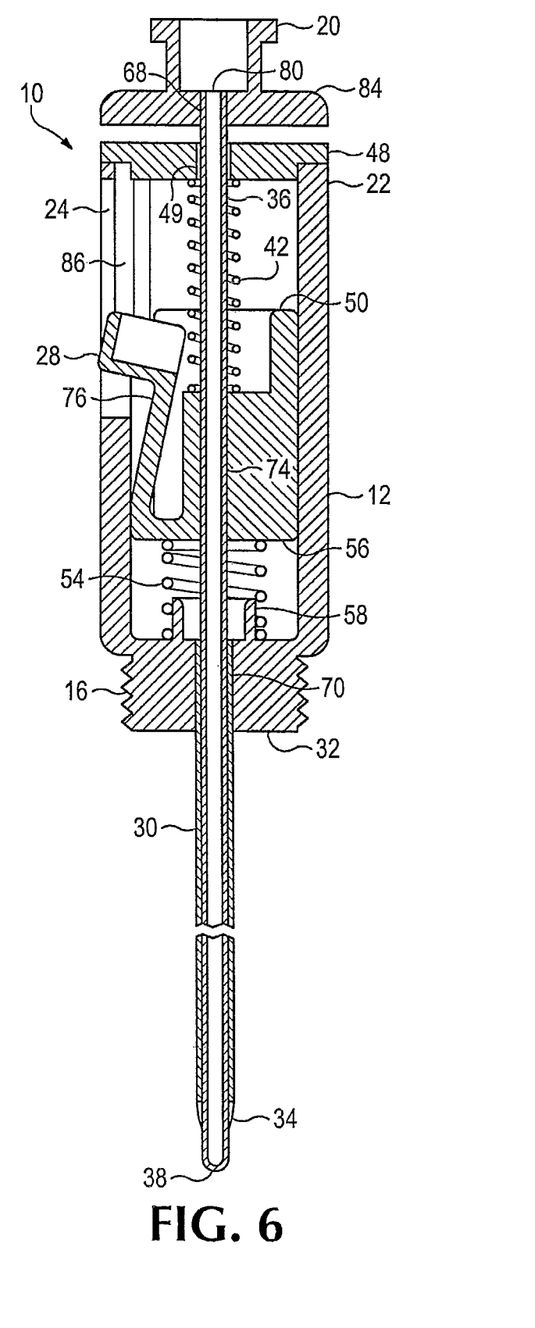
FIG. 6 is a sectional view similar to FIG. 4, but showing the medical instrument with the tubular stylet unlocked and able to be displaced into the sharpened end of the cannula.

As may be seen in FIGS. 4 and 6, the latch release button 28 is movable with respect to the remainder of the carrier 50 by flexing the portion 76, also shown in FIG. 2, so that the stylet pusher 50 can be inserted into the interior of the body 12, and then relaxing it to permit the latch release button 28 to protrude through the longitudinal slot 24, after which the cap 48 can be attached fixedly to the proximal end 22 of the body 12, where it may be secured adhesively, by ultrasonic welding, or by other suitable means.

In the condition shown in FIG. 4, with the carrier or stylet pusher 50 latched in its furthest distal position, the blunt distal end 38 of the stylet 36 protrudes beyond the sharp point 34 of the cannula 30, thus obscuring the sharp point 34 and exposing the opening 40 as a pathway for gas to proceed into and through the interior bore of the stylet 36.

Figures 7, 8, 9:
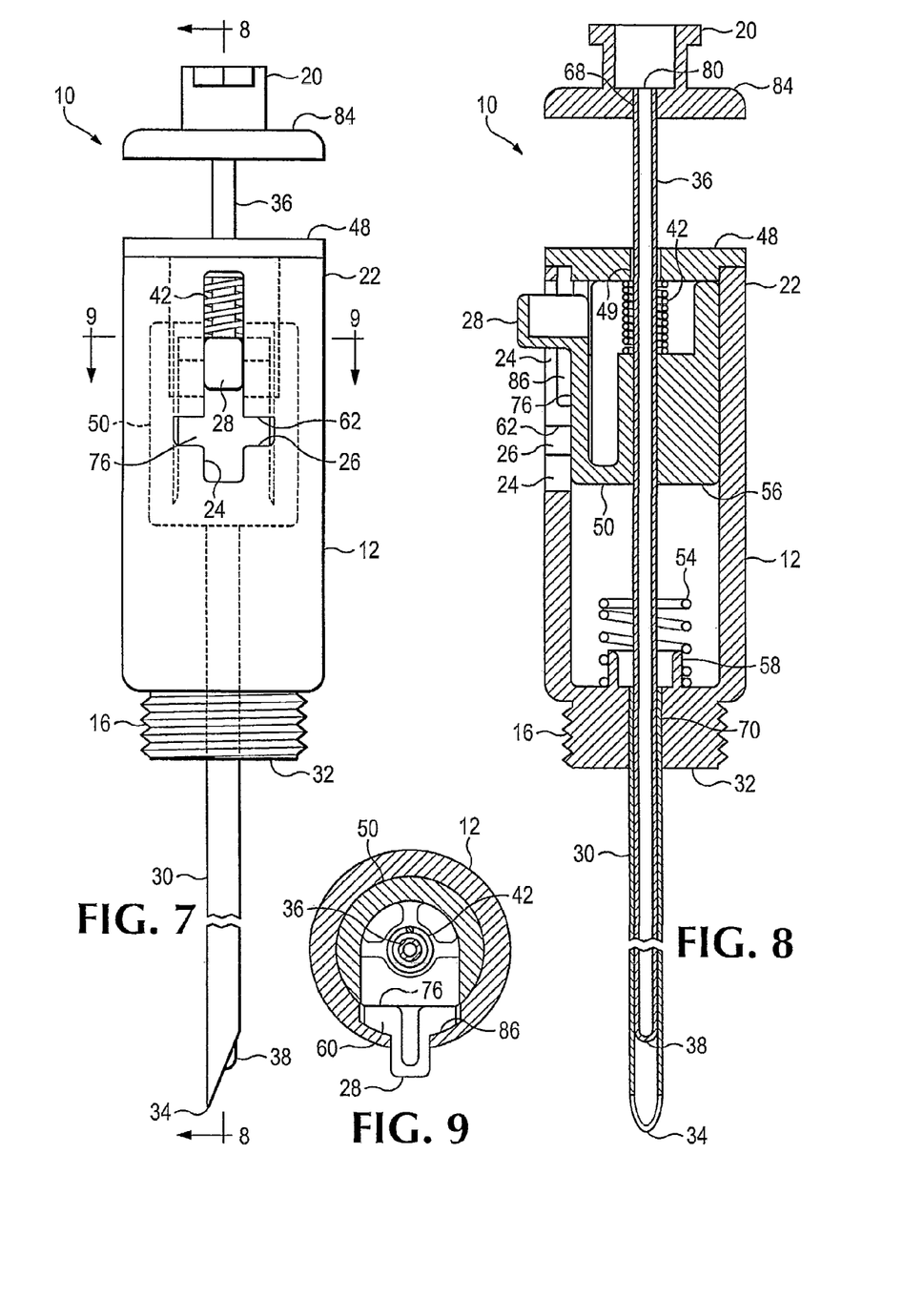
FIG. 7 is a front elevational view of the medical instrument shown in FIGS. 1-6, showing the tubular stylet moved far enough into the cannula to permit use of the instrument to pierce a chest wall of a patient.
FIG. 8 is a sectional view taken along the line 8-8 in FIG. 7, but showing the instrument with the tubular stylet moved into the cannula to the furthest position available.
FIG. 9 is a sectional view taken along line 9-9 in FIG. 7.

The locking mechanism is capable of existing in two states, the locked or protective state shown in FIG. 4, and an unlocked or retracted state as shown in FIGS. 6, 7, and 8. Beginning locked as shown in FIG. 4, the latch release button 28 may be pressed radially inward as shown in FIG. 6, releasing the arms 60 from engagement against the retaining surfaces 62, permitting the stylet pusher 50 to move proximally, as urged by the spring 54, overcoming the force of the spring 42. As shown in FIGS. 7 and 8 the latch release button 28 has been released, allowing the flexible portion 76 to return the arms 60 radially outwardly to reside respectively in the grooves 86, as also shown in FIG. 9, on each side of the longitudinal slot 24. As may be seen in FIG. 6, the spring 54 is expanded longitudinally nearly to its full length when the arms 60 move proximally beyond their positions of engagement with the surfaces 62, but the longer, smaller-diameter spring 42 has been compressed slightly more, and urges the carrier 50 in a distal direction, thus keeping the blunt distal end 38 of the stylet 36 protruding slightly beyond the sharp end 34 of the cannula 30.

When the latch release button 28 is not locked with the arms 60 in the crosswise slot 26, the spring 42 ordinarily urges the stylet pusher 50, and thus the stylet 36, to the position shown in FIG. 6, where its movement in the distal direction is limited by the stronger spring 54.

To relieve a tension pneumothorax, the user penetrates the chest wall with the device 10. When the decompression needle 10 is being urged through a chest wall or abdominal wall the tip 38 is moved in a proximal direction far enough to expose the sharp pointed end 34 of the cannula 30, as shown in FIG. 7, and this causes the latch release button 28 to move proximally in the slot 24. The cannula 30 can then cut and pass through the chest wall tissue, and the position of the blunt distal tip 38 can be determined by observation of the position of the latch release button 28 along the longitudinal slot 24. Once the chest wall has been penetrated, the spring 42 returns the tubular stylet 36 to its extended position, shielding underlying organs from the sharp pointed tip 34 of the outer cannula 30. The user, observing the return of the stylet 36 to its extended position, can then press on the pushbutton 84, or the latch release button 28, moving the stylet pusher 50 against the force of the spring 54 and camming the arms 60 against the interior of the body 12. This flexes the portion 76 to engage the arms 60 in the crosswise slot 26, placing the device 10 into the locked, safe, condition.

Once the chest decompression device 10 is in place, a locking mechanism can thus be engaged to hold the protective tubular stylet 36 extended, keeping the blunt tip 38 exposed and obscuring the sharp tip 34. The needle could then be left in place without fear of the spring biased protective blunt tip retracting if forced into contact with underlying organs.

The connector 20 shown in FIGS. 1-7 may be used to receive a Luer fitting including a check valve allowing air and other fluids to be expelled from within a patient's body cavity via the opening 40 near the blunt tip end 38 and through the interior bore of the inner tube 36 but preventing an open pneumothorax condition from being formed by use of the device 10. An appropriate fitting for a flexible tube may also be attached to the connector 20 as a conduit to provide insufflating gas for use of the device 10 in connection with laparoscopic surgery.

As shown in FIG. 8, the blunt distal end 38 of the inner tube or stylet 36 is located fully within the bore of the cannula 30, and the stylet pusher 50 is in its furthest available proximal position within the interior of the body 12, as might result from intrusion of a plug of tissue into the bore of the cannula 30 and pushing the blunt tip 38. The pusher 50 has compressed the spring 42 and carried the latch release button 28 to the proximal end of the longitudinal slot 24, allowing the spring 54 to extend itself fully in a proximal direction from the distal end 32 of the body 12. This results in the pushbutton 84 and Luer fitting 20, attached to the proximal end 80 of the stylet 36, being moved in a proximal direction away from the end cap 48.

The locking mechanism can be released when that is desired, by pressing on the latch release button 28 to disengage the arms 60 from the retaining surfaces 62 of the transverse slot 26. Once the device 10 has been used, it can be placed into the locked, protracted state, providing safety from sharps danger in a simple yet reliable manner particularly valuable in non-hospital situations such as military environments.

A safety decompression needle 10 has distinct advantages over a Veress needle of the conventional configuration:

(1) By placing the inner tubular stylet 36 into the protracted state and engaging the locking mechanism, the inner tubular stylet 36 is prevented from retracting, and thus the sharp tip 34 of the outer cannula 30 cannot be exposed. This prevents inadvertent puncture of internal organs or other tissues.

(2) When the user determines that a clog exists within the cannula 30, but the bias of the spring 42 on the inner tubular stylet 36 is insufficient to overcome the resistance of the impacted tissue or blood, the user can press on the pushbutton 84, urging it, the stylet pusher 50, and the stylet 36 in a distal direction as a plunger. With the added force, the stylet 36 would likely overcome the resistive forces of the wedged tissue, dislodging the clog. To keep the stylet 36 protracted, the locking mechanism can then be engaged by moving the pushbutton 84 further. As the arms 60 approach the crosswise slot 26, inclined cam surfaces 64 urge them inward, flexing the flexible portion 76 of the stylet pusher 50 inward until the arms 60 move in a distal direction far enough to move resiliently outward into the crosswise slot 26 and come to bear on the retaining surfaces 62.

(3) When the device 10 is locked in the protracted state, the sharp end 34 is safe without a separate cover.

Figure 10:
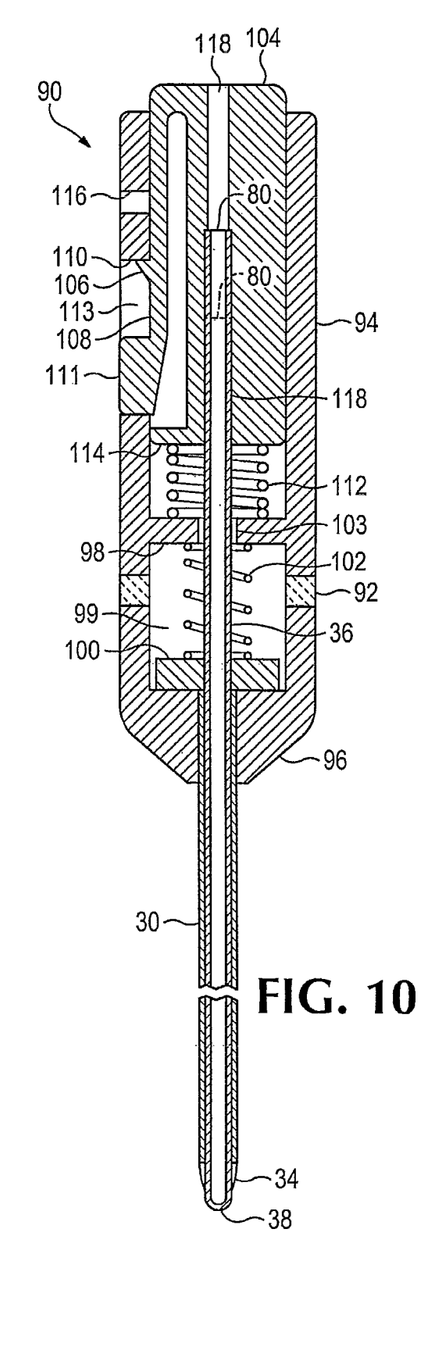
FIG. 10 is a sectional view of a device which is a variation of the medical instrument shown in FIGS. 1-7.

Referring to FIG. 10, a device 90 that is a variation of the device 10 shown in FIGS. 1-9 includes generally cylindrical, pen-like body 94 with a window 92 of transparent material through which the operator may view the inner tubular stylet 36. In a distal end portion 96 of the body 94, a cannula 30 is mounted in a manner similar to the attachment of the cannula 30 to the distal end portion 32 of the body 12 of the device 10. A partition 98 defines a cavity 99 within the distal end portion of the body 94. A colored washer-like collar, or bobber, 100, is securely attached to the tubular stylet 36 within the cavity 99 and functions as a stylet pusher, so that when the force of a helical compression spring 102, surrounding the stylet 36 and extending between the partition 98 and the stylet pusher bobber 100, is overcome, and the sharpened tip end 34 of the outer cannula 30 is exposed, the colored stylet pushing collar 100 is visible to the user through the window 92. The location and size of the window 92 may be designed to make the stylet pusher collar 100 visible with the blunt end 38 in a desired position or range of positions with respect to the sharpened tip 34 of the cannula 30.

As shown in FIG. 10, however, the inner tubular stylet 36 is fully extended, with its blunt end 38 extending beyond the sharpened outer tip 34 of the cannula 30, and the stylet pusher collar 100 is not visible to the operator, but is located within an opaque portion of the body 94.

As shown in FIG. 10, the inner tubular stylet 36 extends through the partition 98, and is movable within a bore 118 defined in a pushbutton 104, shown latched in a locked position with respect to the body 94, in which the pushbutton 104 acts as a positively engaged stylet pusher and keeps the inner tubular stylet 36 extended with its blunt end 38 protruding beyond the sharpened end 34 of the cannula 30.

A catch 106 carried on a resiliently flexible finger portion 108 of the pushbutton 104 is engaged in a distal catch receptacle 110. With the pushbutton 104 so latched, the engagement of the proximal end 80 of the inner tube or stylet 36, against a seat within the bore 118 in the pushbutton 104 keeps the stylet 36 extended to the position shown in FIG. 10 in which its outer blunt end 38 extends beyond the sharpened distal tip 34 of the outer cannula 30, preventing the sharpened tip 34 from puncturing tissues. The catch 106 can be released from the receptacle 110 by pushing a latch release button 111 inward in a slot 113 in the body 94, flexing the finger 108.

Another helical compression spring 112 is located within the body 94, between the proximal side of the partition 98 and the distal end 114, or base, of the pushbutton 104, urging the pushbutton 104 in a proximal direction, within the body 94, that is, upward in FIG. 10. When the pushbutton 104 is not latched in the locked position as shown in FIG. 10, the catch 106 is normally engaged in a proximal catch receptacle 116, and the spring 112 extends by virtue of its own elasticity, urging the pushbutton 104 in a distal direction to keep the catch 106 engaged in the proximal catch receptacle 116, as with the pushbutton 128 shown in FIG. 11. With the pushbutton 104 not in the locked position shown in FIG. 10 the inner tube or stylet 36 is free to move longitudinally within the bore 118 defined centrally and extending longitudinally through the pushbutton 104, with the proximal end 80 movable within the bore 118 between the position shown in solid line and the position shown in broken line, as the stylet 36 is urged by the spring 102 or pressure on the blunt end 38.

Ordinarily, when the cannula 30 of the device 90 is not being urged through tissue by a user, the spring 102 will push the collar or stylet pusher 100 in a distal direction to the distal end of the cavity 99, thus moving the stylet 36 in the distal direction and causing the blunt distal end 38 to protrude as shown in FIG. 10. The colored stylet pusher 100, in its spring-biased position in the cavity 99, is then hidden, obscured by an opaque portion of the plastic housing and indicating to the user that successful placement of the cannula 30 has been made.

However, if during penetration of the chest wall the cannula 36 has become occluded with a tissue plug and the protective tubular stylet 36 is thus kept within the outer cannula 30, the colored stylet pusher 100 remains visible through the window 92. The user may then press on the pushbutton 104 extending from the top or proximal end of the plastic body 94, thus dislodging the tissue core. If the colored stylet pusher 100 is visible in the window 92, revealing that the blunt tip 38 is retracted within the sharp cannula 30, the user might not know whether this is due to a tissue core plug or whether the needle or cannula 30 has not penetrated completely through the chest wall. In this case, the pushbutton 104 can be pushed. If what is judged to be enough force doesn't move the colored stylet pusher 100 out of sight, the chest wall has likely not been penetrated.

Once the user concludes that the sharpened end 34 of the outer cannula has passed through the chest wall, as when the colored stylet pusher 100 disappears, the pushbutton 104 may be pushed to the position shown in FIG. 10 to place the device in the locked state, preventing the sharpened end 34 from further cutting or piercing an internal organ unintentionally.

Figure 11:
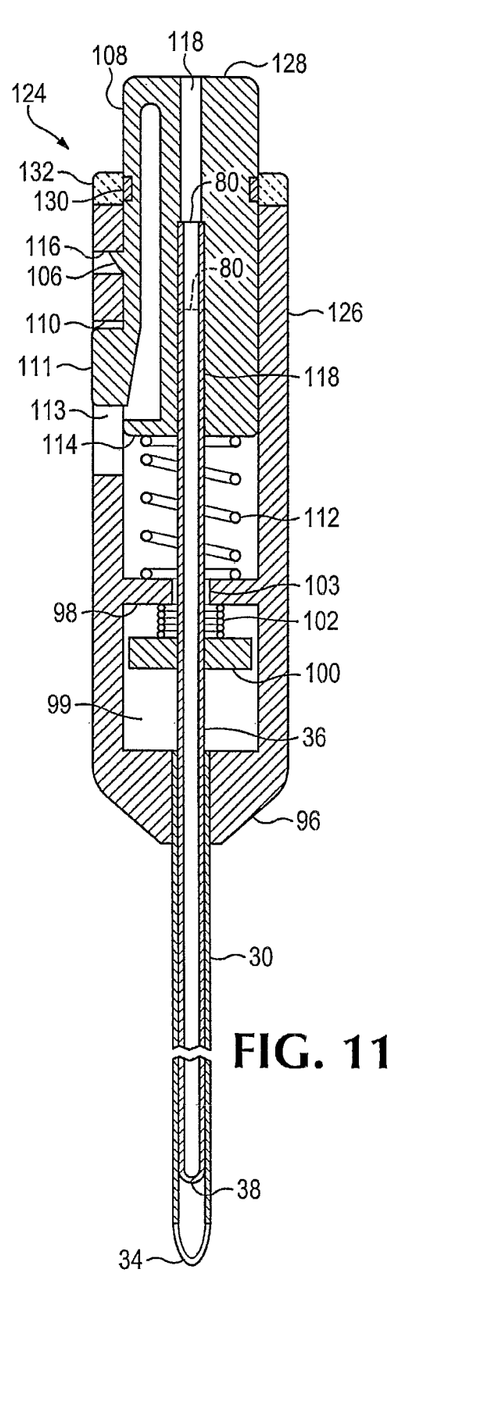
FIG. 11 is a sectional view of a medical instrument which is a variation of the medical instrument shown in FIG. 10.

Referring next to FIG. 11, a device 124 is similar in many respects to the device 90. A body 126 is similar in many respects to the body 94, and a pushbutton 128 is similar in most respects to the pushbutton 104 of the device 90, but the pushbutton 128 of the mechanism of the housing 126 includes a colored collar or layer 130. When the locking mechanism is engaged holding the pushbutton 128 in the locked configuration (protracted state), with the pushbutton 128 in a distal location similar to that of the pushbutton 104 as shown in FIG. 10, the colored collar or layer 130 is not visible. When the locking mechanism is not engaged and the pushbutton 128 is in the retracted state, as shown in FIG. 11, the colored band 130 is visible through a transparent portion 132 of the body 126 and the spring 112 is extended, keeping the pushbutton 128 in its retracted, proximal position as shown in FIG. 11 with the catch 106 in the proximal latch receptacle 116 of the housing, or body 126. When the locking mechanism is in the retracted state as shown in FIG. 11, with the colored band 130 visible, the user can conclude that the sharp tip 34 may be exposed and cannot be assumed to be obscured by the blunt end 38 of the tubular stylet 36.

As shown in FIG. 11, the collar or stylet pusher 100, securely attached to the inner tube or stylet 36, is normally urged by the spring 102 toward a distally located, extended position in which the blunt outer tip 38 of the stylet 36 extends beyond the sharpened outer end 34 of the cannula 30. With the pushbutton 128 in its proximally located retracted position, however, the inner tube or stylet 36 is free to move axially except as urged in a distal direction by the spring 102, so that the stylet 36 may be pushed inward as the device 124 is pushed through a patient's chest wall, and the sharpened end 34 of the cannula 30 is exposed and able to pierce the chest wall. The proximal end 80 of the inner tube or stylet 36 is free to move axially within the bore 118 defined within the pushbutton 128 as the spring 102 is compressed and the inner tube of stylet 36 is urged into and along the interior of the bore of the cannula 30 between the position shown in broken line and the position shown in solid line.

A connector such as the Luer fitting receptacle 20 could be included at the proximal end of the pushbutton 104 or 128.

It will be understood by the reader that a device similar to a combination of the devices 90 and 124 might include all of the colored collar 100, the viewing window 92, the viewing window 132, and the colored band or collar 130, so that the user might discern both that the inner tube or stylet 36 is free to move, as indicated by alignment of the colored band 130 with the viewing window 132, and that the inner tube or stylet 36 may have been forced into the bore of the outer cannula, if the collar 100 is seen to be aligned with the viewing window 92.

Figure 12:
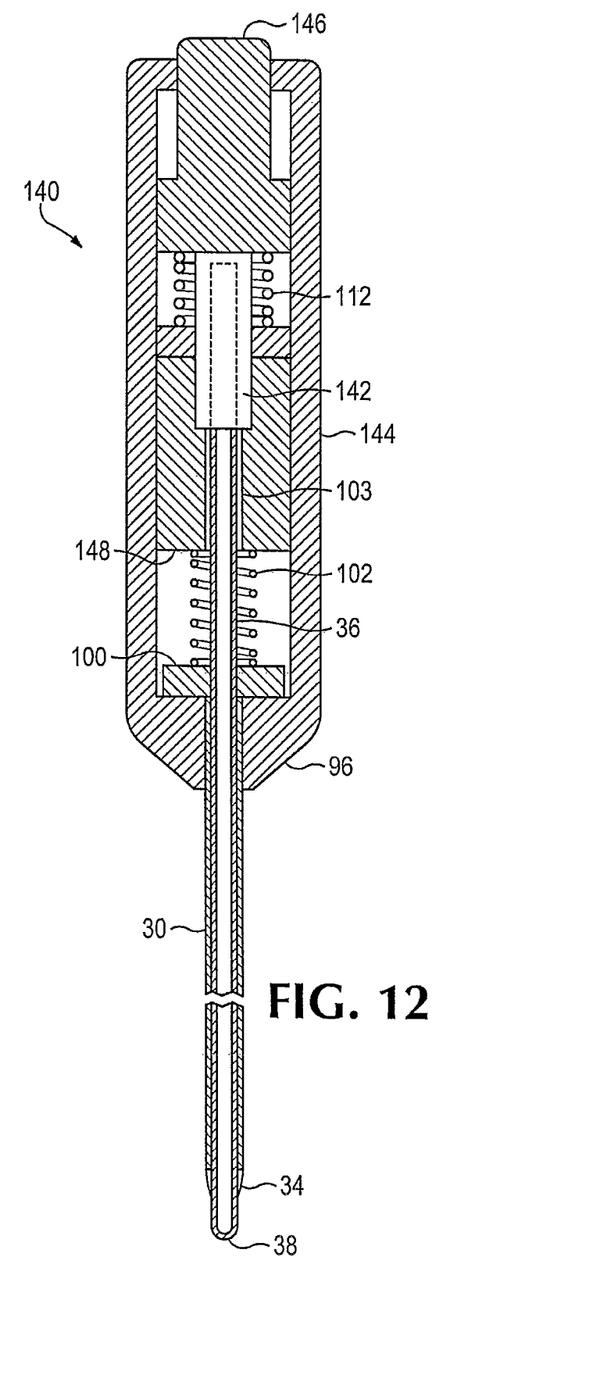
FIG. 12 is a partially schematic sectional view of a medical instrument which is yet a further variation of the medical instruments shown in FIGS. 1-9, 10, and 11.

As shown in FIG. 12, another emergency chest decompression device 140 intended for use in relieving a tension pneumothorax may be generally similar to the devices 90 and 124 shown in FIGS. 10 and 11 but may include a different locking mechanism 142, shown schematically within a body 144 and operable by a pushbutton 146. Within the body 144, there may be a spacer or core 148 defining a space for inclusion of the locking mechanism 142 and acting as a retainer for the proximal end of the spring 102 acting on the collar 100 to urge the inner tube or stylet 36 in a distal direction as in the devices described above and shown in FIGS. 10 and 11. The mechanism 142 may be disposed around the stylet 36, and a loose fit of or a passage through the pushbutton 146 may allow passage of fluid via the stylet 36.

One specific type of locking mechanism is exemplified by standard pushbutton retractable pen tip mechanism, such as the mechanism disclosed in Snell et al. (U.S. Pat. No. 4,991, 988) in which a spring biases two small sets of cams together, and the user is able to extend and lock the pen tip and thereafter release it by repeatedly depressing the pushbutton on the head of a pen. Depressing the pushbutton moves the cams along the pen's long axis, guided by grooves internal to the pen body. The cams rotate with respect to each other and create two discrete pen phases: extended (locked), and retracted (unlocked).

In the retracted state, a base piece of the mechanism 142 is moved farther away from the proximally terminating end of the inner tubular stylet 36, allowing it to be moved into the cannula 30.

In the locked, or protracted, state, the base piece moves closer to and ideally abuts against the proximally terminating end of the inner tubular stylet 36.

Thus, the blunt-ended tubular stylet 36 also has two possible states:

First, when the locking mechanism 142 exists in the retracted state, the stylet 36 is free to travel inward along the longitudinal axis of the outer cannula 30 provided that a force great enough in magnitude to overcome the force of the spring 102 also exists.

Second, when the locking mechanism 142 exists in the locked, or protracted, state, the base piece ideally abuts against the proximally terminating end of the tubular stylet 36. This prevents the inner tubular stylet 36 from moving with respect to the outer cannula 30, regardless of the magnitude of force applied to the distal end 38 of the inner tubular stylet 36.

A further feature of the invention could be a locking mechanism which prevents accidental triggering of the pen click feature. The mechanism that releases the device to its sharp activated mode could have a removable cover, a slide that covers the release mechanism, a hinged door that reversibly covers the release mechanism, or one of a number of other protective mechanisms.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A medical device, comprising:
   (a) a body having a distal end, a proximal end, a length and a longitudinal axis;
   (b) a cutting cannula, mounted fixedly on the body and extending away from the distal end of the body, the cutting cannula having a longitudinal bore and a sharpened distal end;
   (c) a tubular stylet extending through the bore of the cutting cannula, the stylet having a proximal portion and a blunt distal end;
   (d) a stylet pusher disposed within the body and movable longitudinally with respect to the body, the stylet pusher being located with respect to the tubular stylet so as to urge the tubular stylet longitudinally within the bore of the cutting cannula toward the distal end of the cutting cannula;
   (e) a spring housed within the body and arranged to urge the stylet pusher in a distal direction with respect to the body; and
   (f) a selectively engageable and releasable locking mechanism operable first to lock the tubular stylet only in a distally extended position with respect to the body and thereby to keep the tubular stylet in a position in which the blunt distal end of the tubular stylet protrudes beyond the sharpened distal end of the cutting cannula and obscures the sharpened distal end of the cutting cannula when the locking mechanism is engaged, and, second, when the locking mechanism is unlocked, operable to allow both spring-urged extension of the tubular stylet toward a distal position and repression of the tubular stylet in a proximal direction sufficiently to expose the sharpened distal end of the cutting cannula, the locking mechanism including a latch receptacle including a transverse slot, defined in a wall of the body and defining a retaining surface, and an arm extending as a latching member from a flexible portion of the stylet pusher and extending selectively into the transverse slot so as to engage the retaining surface, thereby selectively engaging the locking mechanism.

2. The medical device of claim 1 including a pushbutton located at the proximal end of the body attached to the tubular stylet and thus able to move the tubular stylet longitudinally through the cutting cannula to the distally extended position in which the blunt distal end of the stylet protrudes beyond the sharpened distal end of the cutting cannula.

3. The medical device of claim 1 including a second spring carried in the body and arranged to urge the stylet pusher toward the proximal end of the body and thus urge the tubular stylet toward the proximal end of the body far enough to prevent unintentional engagement of the locking mechanism.

4. The medical device of claim 1 wherein the tubular stylet defines an opening, proximate its blunt distal end, that is exposed and communicates between the interior of the hollow tubular stylet and a surrounding space when the stylet protrudes beyond the sharpened end of the cutting cannula.

5. The medical device of claim 1 wherein the spring housed within the body acts on the stylet pusher, thereby urging the hollow tubular stylet longitudinally through the bore of the cutting cannula toward the distally extended position in which the blunt distal end of the tubular stylet protrudes beyond the sharpened distal end of the cutting cannula.

6. The medical device of claim 1 wherein the stylet pusher is attached to the tubular stylet at a location that is proximal with respect to a proximal end of the cutting cannula and wherein the medical device includes a connector adapted to receive and attach a flow-controlling item to the proximal end of the tubular stylet.

7. The medical device of claim 1 wherein the body defines a longitudinally oriented slot and a portion of the stylet pusher protrudes outwardly from within the body through the slot.

8. The medical device of claim 7 wherein the portion of the stylet pusher protruding through the slot includes a latch release button arranged to be engaged by a user to push the stylet pusher and thereby push the tubular stylet longitudinally in a distal direction within the bore of the cutting cannula.

9. A medical device, comprising:
   (a) a body having a distal end, a proximal end, a length, and a longitudinal axis;
   (b) a cutting cannula, mounted on the body and extending away from the distal end of the body, the cutting cannula having a longitudinal bore, a proximal end open to an interior of the body, and a sharpened distal end;
   (c) a tubular stylet extending through the bore of the cutting cannula, the stylet having a proximal portion and a blunt distal end;
   (d) a pushbutton disposed partially within the body and movable longitudinally of the body, the pushbutton being located with respect to the tubular stylet so as to be able to urge the tubular stylet longitudinally through the cutting cannula toward the distal end of the cutting cannula, and a portion of the pushbutton protruding longitudinally out from the proximal end of the body;
   (e) a selectively engageable and releasable locking mechanism arranged to hold the tubular stylet in a distally extended position with respect to the body and thereby to keep the tubular stylet in a position in which the blunt distal end of the tubular stylet protrudes beyond the sharpened distal end of the cutting cannula and obscures the sharpened distal end of the cutting cannula when the locking mechanism is engaged; and
   (f) an indicator member attached to the pushbutton at a location within the body, and wherein the body includes a transparent portion through which the indicator member is visible when the distal end of the tubular stylet is movable relative to the cutting cannula and the sharpened end of the cutting cannula may be exposed.

10. The medical device of claim 9 including a colored collar member attached to the tubular stylet at a location on the tubular stylet within the body and proximal to a proximal end of the cutting cannula, the collar member being movable together with the tubular stylet, and wherein the body includes a transparent window, with which the collar member is aligned and through which the collar member is visible only when the tubular stylet is in a predetermined position relative to the cutting cannula, as a visual indication that the sharpened distal end of the cutting cannula is exposed.

11. The medical device of claim 9 including a stylet pusher attached to the stylet and a visibly identifiable position indicator located on the stylet pusher and within the body, and wherein the body includes a transparent window through which the position indicator is visible only when the stylet pusher is in a retracted position in which the stylet pusher does not hold the tubular stylet in a protracted position obscuring the sharpened distal end of the cutting cannula.

12. The medical device of claim 9 including a stylet pusher and wherein the body includes a transparent window, wherein the stylet pusher is attached to the tubular stylet at a location proximal to a proximal end of the cutting cannula, wherein a portion of the stylet pusher is visible through the window, and wherein the visible portion of the stylet pusher indicates whether the blunt distal end of the tubular stylet protrudes beyond the sharpened distal end of the cutting cannula and obscures the sharpened distal end of the cutting cannula.

13. The medical device of claim 9 further including a stylet pushing collar mounted on the tubular stylet and located within the body and proximal to a proximal end of the cutting cannula, and wherein the body includes a transparent window through which the stylet pushing collar is visible only when the blunt distal end of the tubular stylet is in a predetermined range of positions with respect to the sharpened distal end of the cutting cannula.

14. A medical device, comprising:
(a) a body having a distal end, a proximal end, a length and a longitudinal axis;
(b) a cutting cannula, mounted on the body and extending away from the distal end of the body, the cutting cannula having a longitudinal bore and a sharpened distal end;
(c) a tubular stylet extending through the bore of the cutting cannula, the stylet having a proximal portion and a blunt distal end;
(d) a stylet pusher located in the body, interconnected with the tubular stylet and movable longitudinally of the body so as to move, and move with, the tubular stylet,
(e) a spring located within the body, and acting on the stylet pusher so as to urge the tubular stylet longitudinally through the longitudinal bore of the cutting cannula toward the distal end of the cutting cannula;
(f) a pushbutton located at the proximal end of the body and extending outward therefrom, the pushbutton being movable longitudinally within the body and arranged to push the stylet in a distal direction within the cutting cannula;
(g) a selectively engageable and releasable locking mechanism arranged to hold the pushbutton in a selected position with respect to the body and thereby to keep the tubular stylet in a position in which the blunt distal end of the tubular stylet protrudes beyond the sharpened distal end of the cutting cannula and obscures the sharpened distal end of the cutting cannula when the locking mechanism is engaged;
(h) a visibly identifiable position indicator located on the pushbutton and within the body; and
(i) a transparent portion included in the body, through which the position indicator is visible only when the pushbutton is in a retracted position in which the pushbutton does not hold the tubular stylet in a position obscuring the sharpened distal end of the cutting cannula.

* * * * *